(12) United States Patent
Rubin et al.

(10) Patent No.: US 6,701,928 B2
(45) Date of Patent: Mar. 9, 2004

(54) INHALER DISPENSING SYSTEM ADAPTERS FOR LARYNGECTOMIZED SUBJECTS AND ASSOCIATED METHODS

(75) Inventors: Bruce Kalman Rubin, Winston-Salem, NC (US); Christopher Sung Wang, Winston-Salem, NC (US)

(73) Assignee: Wake Forest University, Winston-Salem, NC (US)

( * ) Notice: Subject to any disclaimer, the term of this patent is extended or adjusted under 35 U.S.C. 154(b) by 188 days.

(21) Appl. No.: 09/822,992

(22) Filed: Mar. 30, 2001

(65) Prior Publication Data

US 2001/0035182 A1 Nov. 1, 2001

Related U.S. Application Data

(60) Provisional application No. 60/195,014, filed on Apr. 6, 2000.

(51) Int. Cl.[7] .................... A61M 16/00; A62B 9/06
(52) U.S. Cl. ......................... 128/207.14; 128/203.12; 128/200.23
(58) Field of Search ............... 128/200.26, 203.12, 128/203.15, 207.14–207.18, 200.23

(56) References Cited

U.S. PATENT DOCUMENTS

| | | | | |
|---|---|---|---|---|
| 3,088,466 A | * | 5/1963 | Nichols | 128/207.14 |
| 3,443,564 A | * | 5/1969 | Oehmig | 128/204.14 |
| 3,707,301 A | * | 12/1972 | Rauls | 285/9 |
| 3,789,843 A | | 2/1974 | Armstrong et al. | |
| 3,924,636 A | * | 12/1975 | Addison | 128/207.14 |
| 3,973,569 A | * | 8/1976 | Sheridan et al. | 128/207.14 |
| 4,015,608 A | * | 4/1977 | Rogers | 128/207.14 |
| 4,291,688 A | | 9/1981 | Kistler | |
| 4,534,343 A | * | 8/1985 | Nowacki et al. | 128/200.23 |
| 4,596,248 A | * | 6/1986 | Lieberman | 128/207.16 |
| 4,627,433 A | * | 12/1986 | Lieberman | 128/207.16 |
| 5,042,467 A | | 8/1991 | Foley | |
| 5,042,468 A | * | 8/1991 | Lambert | 128/200.26 |
| 5,048,518 A | * | 9/1991 | Eliachar et al. | 128/207.14 |
| 5,078,131 A | * | 1/1992 | Foley | 128/203.15 |
| 5,107,828 A | * | 4/1992 | Koss et al. | 128/200.26 |
| 5,181,505 A | * | 1/1993 | Lew et al. | 128/200.26 |
| 5,217,008 A | * | 6/1993 | Lindholm | 128/207.14 |
| 5,263,922 A | * | 11/1993 | Sova et al. | 602/59 |
| 5,287,852 A | * | 2/1994 | Arkinstall | 128/207.14 |
| 5,368,016 A | * | 11/1994 | Henry | 128/200.23 |
| 5,438,982 A | * | 8/1995 | MacIntyre | 128/207.14 |
| 5,520,174 A | * | 5/1996 | Evans et al. | 128/207.14 |
| 5,676,129 A | | 10/1997 | Rocci, Jr. et al. | |
| 5,746,197 A | * | 5/1998 | Williams | 128/200.23 |
| 5,826,571 A | | 10/1998 | Casper et al. | |
| 5,848,588 A | | 12/1998 | Foley et al. | |
| 5,950,620 A | * | 9/1999 | Stricklin | 128/202.28 |
| 6,378,521 B1 | * | 4/2002 | Van Den Berg | 128/207.14 |

OTHER PUBLICATIONS

Trudell Medical International AeroChamber Valved Holding Chamber Product described at http://www.trudellmed.com/TMIAero.html (Mar. 16, 2000).

* cited by examiner

*Primary Examiner*—Weilun Lo
*Assistant Examiner*—Joseph F. Weiss, Jr.
(74) *Attorney, Agent, or Firm*—Myers Bigel Sibley & Sajovec P.A.

(57) ABSTRACT

Adapters configured to engage with conventional oral inhalers or inhalers with valved-holding chambers for laryngectomized subjects can sealably engage with the mouthpiece of same. The adapter can be configured and sized to slide onto conventional devices. The adapter is configured to enter the opening in the neck of a user a sufficient operative depth to facilitate delivery of the inhalant into the air passage and generally downwardly toward the pulmonary region or lower airway.

35 Claims, 7 Drawing Sheets

INHALER DISPENSING SYSTEM ADAPTERS FOR LARYNGECTOMIZED SUBJECTS AND ASSOCIATED METHODS

FIELD OF THE INVENTION

The present invention is directed to the delivery of inhalant medications to subjects having tracheotomies or tracheotomies, and is particularly directed to the delivery in subjects which have undergone laryngectomies.

BACKGROUND OF THE INVENTION

A typical laryngectomy, and, particularly for a patient which has undergone a laryngectomy because of cancer which has arisen from long-term smoking, involves the removal of a significant portion of the larynx and the introduction of a surgical incision into the trachea via the neck to form a permanent opening in the skin and underlying structure that provides an air passage into the lung(s). In many instances, such a patient will use inhalant-based medications to treat emphysema and/or asthma or other lung deficiencies or airway impairments by directing aerosolized inhalant medications into the opening in the neck. The efficacy of such treatment can depend on the successful delivery of the proper medication dosage or ingredient to the desired region of the lung or airway.

Conventionally, inhalant-based medications such as aerosolized medications can be delivered in several ways. For example, some subjects directly insert a pressurized metered dose inhaler ("pMDI") into or proximate the opening in the neck. However, unlike the oral use where the lips and mouth are able to substantially seal about the end of the pMDI device, the neck opening does not have the structure or control to correspondingly collapse about the device. In an attempt to overcome such a deficiency, others position an infant mask connected to an inhalant aerosolized drug chamber (such as an AeroChamber® connected to a pMDI) over the opening to deliver the medication into the opening. Unfortunately, the infant mask can be somewhat cumbersome and/or inconvenient to use. Furthermore, spraying medication from the pMDI directly into the opening can cause premature deposit of the medication and impede proper delivery as well as potentially injuring the delicate tissue of the trachea. The delivery shortcomings can, in turn, reduce the therapeutic treatment efficacy or value of the drug and potentially introduce undesirable and pathologic changes in the user's airway.

OBJECTS AND SUMMARY OF THE INVENTION

It is therefore a first object of the present invention to provide a more effective and/or relatively convenient method of administering inhalable medications via the opening in the neck for laryngectomized subjects.

It is yet another object of the present invention to provide an improved manner of delivering aerosolized medications to a subject with a tracheotomy (i.e., a subject having a temporary opening formed in the neck) or a tracheostoma (i.e., a subject having a permanent or chronic opening formed in the neck).

It is an additional object of the present invention to provide less irritating, safer, periodic, inhalation-based drug deliveries through openings in the neck (which can be particularly useful for tracheotomy and/or tracheostoma subjects).

It is another object of the present invention to provide a device which can allow laryngectomy subjects to more effectively use off-the-shelf or conventional inhalers and/or inhalers with valved holding chambers or reservoirs.

These and other objects are satisfied by the present invention by an adapter which is in fluid communication with a conventional oral inhalation-based medication dispensing device and which is configured to penetrate the opening and direct the desired medications into a subject's air passage such that it inhibits premature deposit of the medication. Preferably, the adapter alignably engages with the opening in the subject's neck and substantially seals the flow path to more effectively deliver aerosolized medications therein. The adapter is particularly suitable to operate with an aerosolized drug delivery device such as an Aero-Chamber® and/or pMDI.

In a preferred embodiment, the adapter is attached to the AeroChamber® device and is configured with an arcuately shaped profile to direct the flow path (and thus the medication) through the opening and downwardly toward the lungs. The adapter can include a seating spacer (which can be a separate component or integrally formed onto the adapter body) to facilitate proper seating and to facilitate sufficient penetration of the end of the adapter to help reliably position the penetration end of the adapter in the user. The seating spacer can also stabilize the adapter about the user opening during operation. Penetration depth and/or the flow channel size and length of the adapter may be important for influencing air/medication flow direction as well as proper dispersion of the drug into the air passage (inhibiting premature deposit of the drug) and to the desired systemic or target region.

A first aspect of the invention is directed to an adapter for an inhalation based drug dispensing device having a medication dispensing exit flow port and a drug flow path associated therewith for use with a subject having a tracheotomy or a tracheostoma type opening in the neck. The adapter includes a tubular body having opposing first and second end portions and defining a flow path therebetween. The tubular body first end is configured to penetrate a (relatively short) depth into a subject through the opening in the neck such that it resides in the subject's airflow path. The tubular body second end is located external to the user and is configured to engage with the inhalation-based drug dispensing device such that the tubular body flow path is in fluid communication with the drug dispensing device.

In a preferred embodiment, the drug-dispensing device comprises a pressurized metered dose inhaler assembled to a valved-reservoir or holding chamber. In this embodiment, the adapter is configured to engage with the mouthpiece of the valved holding chamber. However, the adapter can be used with the pMDI alone and thus, configured to with the mouthpiece of the pMDI. Preferably, the tubular body has an arcuate profile and in position and during use, the arcuate profile is configured to extend into and penetrate through the opening in the neck and direct the medication from the drug dispensing device generally downwardly into a user's air flow path as it exits the tubular flow path. The adapter can also include a seating spacer as discussed above.

A second aspect of the present invention is an inhaler-based delivery system for administering aerosolized medications to a subject having undergone a laryngectomy and having an associated opening in the neck extending to an internal air flow passage. The system includes a pressurized metered dose inhaler having an aerosol chamber and exit port and an adapter having a tubular body with opposing first and second end portions and an internal flow path extending therebetween. The internal flow path is in fluid communication with the pressurized metered dose inhaler aerosol chamber. The adapter tubular body first end portion is sized and configured to enter into the opening of the laryngectomized user a sufficient distance to direct the inhalant based medication received from the pressurized metered dose inhaler through said adapter internal flow path and generally downwardly into the user's air flow passage toward the user's lower airway.

In a preferred embodiment, the system also includes a valved holding chamber or reservoir with an exit port positioned intermediate the pressurized metered dose inhaler and the adapter, all of which are in fluid communication with each other. The adapter tubular body second end portion is configured to sealably engage with the valved holding chamber or reservoir. Further, the adapter tubular body is preferably configured with an internal profile which has a gradual or reduced profile change and/or a smooth wall along its length (and particularly proximate the flow path at the junction of the adapter and mouthpiece) so as to reduce airflow turbulence attributed to same. As before, it is preferred that the system also include a seating spacer or seating spacer portion operably associated with a perimeter portion of the tubular body, positioned intermediate the first and second end portions such that it is spaced away from the first end portion. In position on the user, the seating spacer portion is configured and sized to reside against the skin of the user external to the opening to define (at least partially) the penetration depth of said first end portion into the opening. Preferably, the adapter tubular body second end portion is configured and sized to slidably engage with one of the pressurized metered dose inhaler or the valved-holding chamber.

An additional aspect of the present invention is a method of using an inhalation-based medication-dispensing device. The method includes the steps of providing an adapter having first and second end portions and an internal flow path therebetween to a laryngectomized subject having an opening in the neck; sliding the adapter second end portion onto the oral inhalation based dispensing device; inserting the adapter first end portion into the user air flow passage through the opening in the neck to a desired penetration depth; activating the inhalation based medication dispensing device to release the inhalant medication; and directing the inhalant medication into the adapter and then into the user air flow passage such that it is oriented generally downwardly toward the user's pulmonary region or lower airway.

Still another aspect is a laryngectomy modification kit for oral inhaler systems, comprising a tubular adapter having opposing first and second end portions, the second end portion configured to slidably engage with a mouthpiece associated with the oral inhaler system. The kit also includes at least one seating spacer. The tubular adapter is configured to be inserted into the opening in the neck of a laryngectomized subject. The kit may include multiple size (and or shaped) seating spacers to allow a more customized fit for a user or multiple disposable seating spacers for easy change out by a user for each adapter.

The present invention allows laryngectomized subjects to more effectively use conventional and/or existing oral inhalers or inhalers with reservoirs or valved holding chambers by configuring the adapter to sealably engage with the mouthpiece of same and providing an easy to use (in a preferred embodiment it is configured such that it can be easily slid onto the conventional devices) extension which allows the adapter to enter the opening in the neck a sufficient operative depth. Indeed, the adapter penetration distance into the air passage is at a sufficient depth so as to facilitate operation of the inhaler even if the trachea collapses during delivery. By configuring easy to use adapters which can conveniently engage with off-the-shelf inhalers, laryngectomized subjects can more effectively employ inhalers directed to conventional oral (mouth) operation.

The foregoing and other objects and aspects of the present invention are explained in the specification set forth below.

DETAILED DESCRIPTION OF PREFERRED EMBODIMENTS

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. In the figures, certain layers, regions, or components may be exaggerated for clarity.

Figure 1:
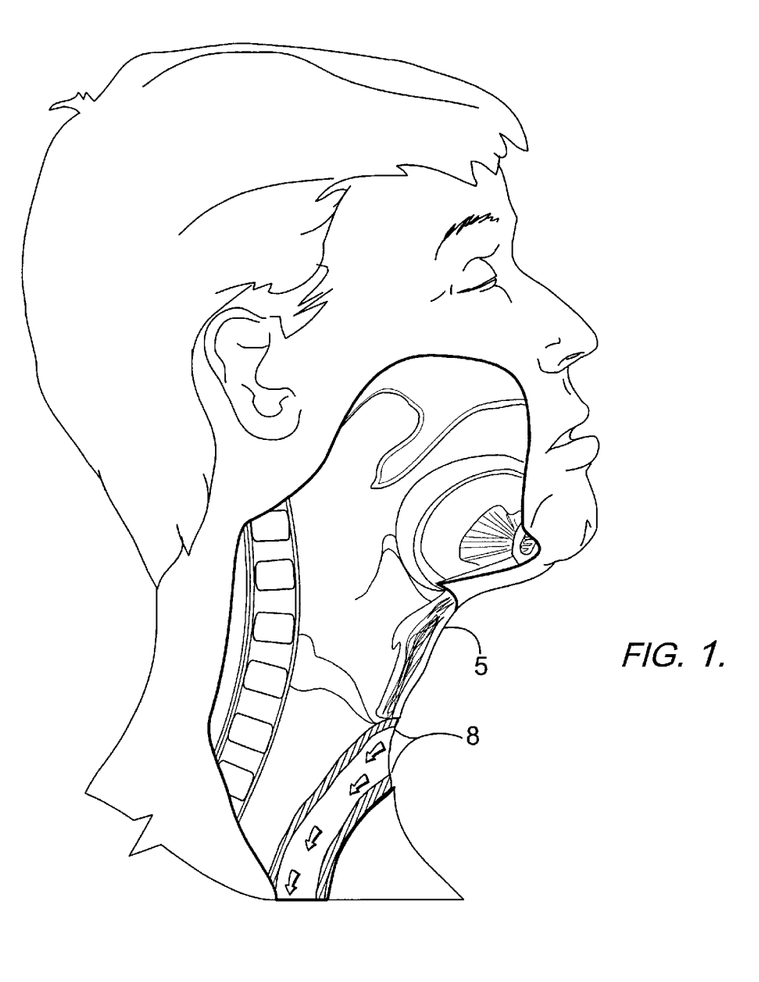
FIG. 1 is a partial cutaway side view illustrating the anatomy of a subject after a laryngectomy.

Generally described, the present invention provides devices, systems, and methods which are directed to improved, more convenient, inhalation-based drug delivery to patients which have a tracheotomy (i.e., a subject having a temporary opening formed in the neck) or a tracheostoma (i.e., a subject having a permanent or chronic opening formed in the neck). The permanent opening 8 typically associated with a subject 5 having undergone a laryngectomy as illustrated in FIG. 1.

The present invention is directed to adapters which are configured to be in fluid communication with conventional inhalation-based medication dispensing devices and which, when in position on a user, are configured to penetrate the opening 8 and direct the desired medications into a subject's air passage such that premature deposit of the medication is inhibited. Preferably, the adapter aligns and engages with the opening in the subject's neck and substantially seals the opening about the adapter body to more effectively deliver inhalable drugs therein. The conventional inhalation-based inhalers can be any suitable type and include pMDI's (pressurized metered dose inhalers) and DPI's (dry powder inhalers).

In a preferred embodiment, the adapter is used to deliver aerosolized medications from pMDI devices. That is, in such an embodiment, the adapters of the present invention are configured to engage with the outlet mouthpieces of conventional aerosolized pMDI devices. The adapters can be sized and configured to sealaby engage to the mouthpiece shape (typically oval, truncated oval, elliptical, or circular). As will be appreciated by those of skill in the art, there are a number of types, size, and configuration pressurized pMDI devices available and the present invention is not limited to any one thereof. Examples of pMDI devices can be found in U.S. Pat. Nos. 3,789,843; 4,291,688; 5,826,571; and 5,676,129, the contents of each of which are hereby incorporated by reference in their entireties as if recited in full herein.

Examples of inhalant-based medicines or drugs which can be delivered according to the present invention include those directed to treat chronic obstructive pulmonary disorder ("COPD"), cystic fibrosis, asthma, emphysema, chronic bronchitis, or other airway or pulmonary deficiencies, conditions, or restrictions. The inhalants can also be directed to treat other systemic targets. For example, this administration concept may be used with locally acting agents such as antimicrobial agents, protease inhibitors, and nucleic acids/oligios as well as systemic agents such as peptides and proteins. More particularly, the inhaler-based delivery can include antimicrobial agents such as antitubercular compounds, proteins such as insulin for diabetes therapy or other insulin-deficiency or resistance related disorders, peptides such as leuprolide acetate for treatment of prostate cancer and endometriosis and nucleic acids or oligonucleotides for cystic fibrosis gene therapy. See e.g. Wolff et al., *Generation of Aerosolized Drugs,* Jnl. Aerosol Med. pp. 89–106 (1994).

In a preferred embodiment, the inhalants administered according to the present invention include bronchodialators and steroid aerosol formulations of excipient containing metered doses held in pre-filled pMDI's comprising albuterol (for example, Ventolin available from Glaxo Wellcome, Research Triangle Park, N.C.) and beciomethasone (for example, Beclovent, also available from Glaxo Wellcome) and many others as is known to those of skill in the art.

Figure 2:
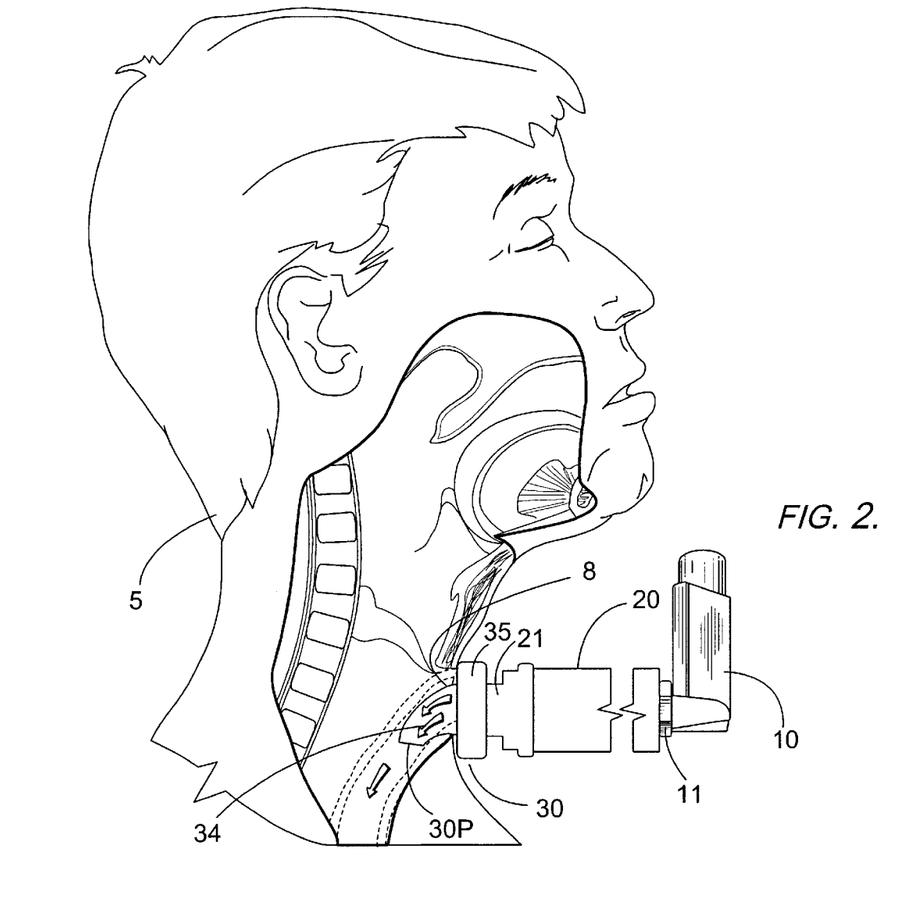
FIG. 2 is a side view of an inhaler-based medication delivery system according to the present invention in which a portion of the system penetrates into the neck opening of a laryngectomized subject.

In one embodiment, as shown in FIG. 2, an adapter 30 of the present invention can be configured to engage a valved-holding chamber or reservoir device 20 which is sealably engaged to a mouthpiece 10*m* of a pMDI 10. The valved holding chamber device 20 is also known to those of skill in the art as a reservoir, an extender device, a spacer, and the like. One particularly suitable valved-holding chamber for aerosolized drug delivery is known as the AeroChamber® and is available from Trudell Medical International (London, Ontario, Canada).

In position on the user 5, as shown in FIG. 2, the adapter 30 is inserted a distance through the opening 8 to direct the flow path 34 (and thus the medication) through the opening 8 and generally downwardly away from the opening toward the lungs or pulmonary region. The adapter 30 can include a seating spacer 35 (which can be a separate component or integrally formed onto the adapter body) to facilitate proper seating against the user's skin proximate the opening 8 and to facilitate sufficient penetration of the end of the adapter to help reliably position the penetration end 30*p* of the adapter in the user. Alternatively, the adapter 30 can be used in isolation of a seating spacer.

Figure 3A:
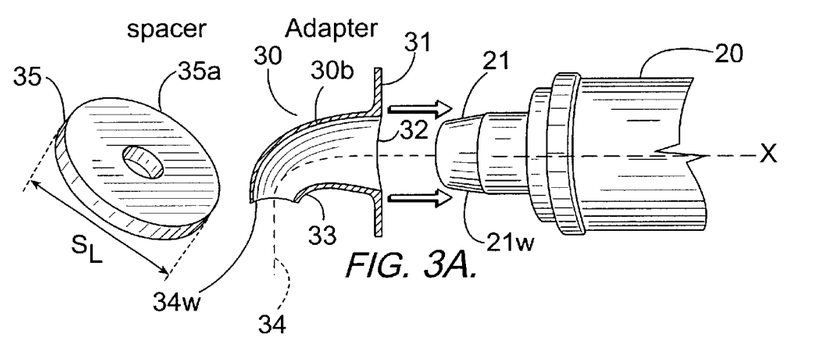
FIG. 3A is a partial cutaway side exploded view of an adapter and seating spacer configured for assembly onto a metered dose inhaler according to the present invention.
Figure 3B:
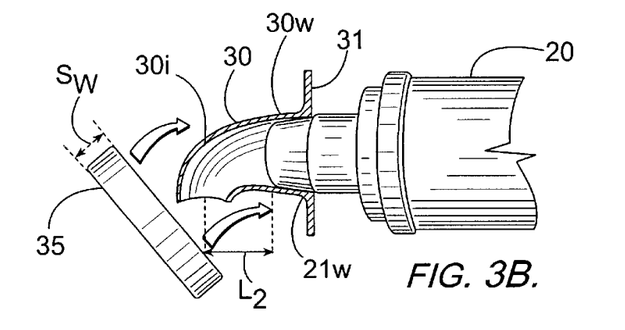
FIG. 3B is a partial cutaway side view of the adapter of FIG. 3A attached to a pressurized metered dose inhaler.
Figure 3C:
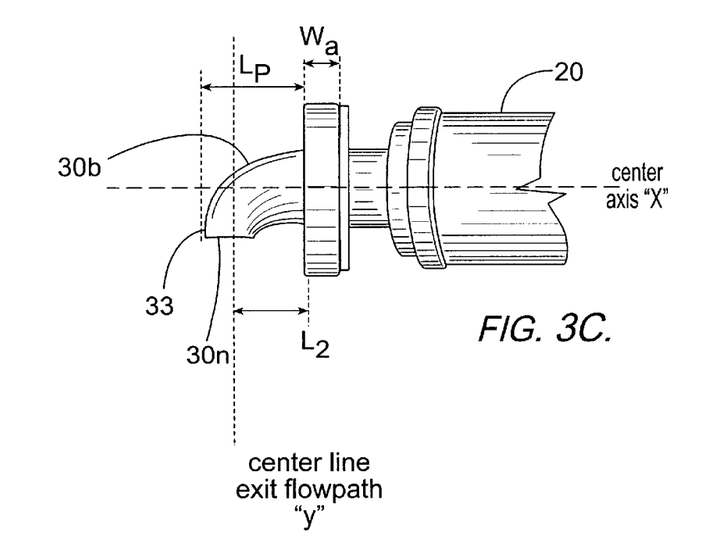
FIG. 3C is a side view of the seating spacer and adapter of FIGS. 3A and 3B mounted onto the pressurized metered dose inhaler unit.

In a preferred embodiment, as shown in FIGS. 3A–3C, the adapter 30 is configured to slide over the end 21 of the valved holding chamber device 20 (preferably, an AeroChamber® or similar type reservoir device) and securely mount to the external wall 21*w* of the device 20 (snugly such that it is substantially sealed thereto). Preferably, as shown in FIG. 3B, the attachment is such that it forms a smooth internal profile 30*ia* for the flow path adjacent the junction of the two devices. Of course, the adapter 30 can also be configured to attach to either the mouthpiece of the inhaler 11 or the end 21 of the valved holding chamber via other attachment means as will be appreciated by those of skill in the art. For example, the adapter 20 can be configured as a "male" component and slide into and engage the inside wall of the valved holding chamber or inhaler mouthpiece (not shown). In addition, a gasket or O-ring or other sealing component can be used to connect the adapter to the drug delivery device (not shown). Other attachment means can also be employed, such as mating threads, quick disconnect fittings, adhesives, and the like, although some of these examples may require customization of the valved holding chamber device 20 (or inhaler 10) which may be more costly than adapter mounting techniques described above in which the adapter 30 can readily attach to the mouthpiece in a manner which allows standardized construction corresponding to conventional oral inhalers.

Turning to FIG. 3A, the adapter 30 includes a tubular body 30*b* with a first end portion 33 (proximate the penetration end 30*p*), an opposing second end portion 32 (proximate the drug flow inlet), and an internal flow path 34 therebetween. Preferably, as shown, the tubular body 30*b* has a curvilinear, and more preferably an arcuate, profile which turns the flow path 34 from the second end portion 32 to the first end portion 33 such that it directs the medication therefrom in a direction which is generally downward when in position in the user. Thus, avoiding the possibility that the tracheal wall will obstruct the outlet of the adapter 30 during inhalation.

As is also shown, it is preferred that the adapter second end portion 32 have a cross-sectional width or area which is greater that the cross-sectional width at the first end portion 33 (i.e., the width of the flow channel narrows along the length thereof). The width of the flow channel 34 proximate the first end portion 33 of the adapter (or the inner diameter of the tubular body thereat) is preferably in the range of from about 8–14 mm for adult users, while the width of the flow channel 34 (and shape/area) at the second end portion 32 is preferably substantially the same as that of the mating mouthpiece 11 or 21 (FIG. 2).

As is shown in FIG. 3A, the internal flow path 34 is preferably configured with a gradual radius of curvature and a smooth inner wall surface to reduce turbulence in the flow path. It is also preferred that the adapter body 30b be sized and configured such that it has a length which is sufficient to assure proper penetration while not being overly long or wide so as to configure the adapter with a limited or decreased amount of "dead volume" in the adapter internal flow path. As shown in FIG. 3C, the tubular body 30b is configured such that the flow path 34 directs the medication such that it exits the flow path at the nozzle or first end portion at a direction which is about 45–90 degrees, and more preferably about 75–90 degrees from the direction it travels as it enters the tubular body proximate the second end portion. This is illustrated by the centerline of the flow path at the entry of the adapter 30 (shown by the line designated as the "X" axis) and the centerline of the flow path at the exit from the tubular body (shown by the line designated as the "Y" axis), the two centerlines being substantially perpendicular to each other.

Preferably, as shown in FIG. 3A, the tubular body second end portion 32 is configured to coaxially align with the mouthpiece 21 (or directly to the pMDI mouthpiece 11). In one embodiment, the mouthpiece 21 and the second end portion of the tubular body 32 have a circular configuration, and the second end portion is mounted to the mouthpiece 21 such that it is concentric to the flow axis of the dispensing body.

FIG. 3B also illustrates a length "$L_2$" which is the average flow path length added to the dispensing path by use of the adapter when the adapter 30 is mounted to be coincident with the mouthpiece portion 21 of the valved holding chamber device 20. The adapter 30 can be configured to mount further onto (deeper) the valved holding chamber device 20 and the tubular body can correspondingly be configured with an additional length to adjust for the deeper alternative mounting configuration. Of course, the reverse is also true, as the tubular body 30b can be mounted to an end portion of the mouthpiece, and the tubular body 30b be configured with a correspondingly lesser length. For an average adult male, the adapter 30 is configured to provide a flow path distance "$L_2$" which is about 20–40 mm, and more preferably about 22–30 mm.

As is also shown by FIGS. 2 and 3C, the tubular body 30b of the adapter 30 extends or penetrates a distance into the user to extend within the user's air flow passage 8p. The distance that the adapter body 30b extends from the opening to the first end 33 of the tubular body in the passage 8p can be described as the penetration length "$L_p$". Although this penetration length may vary somewhat subject to subject primarily due to anatomical considerations such as muscle tone, tissue, bone structure, and the like, it is preferred that the penetration length be sufficient to position the flow path 34 of the adapter within the air passage 8p, and preferably position the flow path such that it is substantially centrally located therein.

In a preferred embodiment, as is also shown in FIGS. 3A–3C, the adapter 30 includes a seating spacer 35. The seating spacer 35 is configured to abut the skin of the user proximate the opening 8 when the adapter 30 is in position during use. As such, the seating spacer 35 can help define the penetration depth of the adapter body 30b as well as the orientation of the flow path 34. Preferably, the seating spacer 35 is tightly held against the external wall 30w of the tubular body in a substantially tight sealing arrangement (operatively acting similar to the oral seal provided by a user's lips). In position on the user, the seating spacer 35 is also configured such that it is also held securely and firmly against the user to also substantially seal and stabilize the device at the opening 8. The seating spacer 35 can thereby facilitate a more efficient delivery of the medication by providing a more secure/sealed inspiratory path about the opening 8 and the adapter 30. In addition, the tubular body 30b alone and more preferably with, the seating spacer 35, can more desirably direct the drug into the air passage 8p and can also inhibit premature deposit of the excipient or active ingredient of the aerosolized formulation about the opening 8.

The thickness or width ($S_W$) of the seating spacer 35 is typically from about 5–20 mm, and preferably about 10 mm. The seating spacer 35 also preferably has a length ($S_L$) which is sufficient to cover the perimeter of the opening 8 and seal and anchor the tubular body 30b thereagainst, Typically the length is about 10–30 mm and is more preferably about 10–25 mm. As the penetration depth of the tubular body 30b can be restricted by the seating spacer 35 as it engages externally with the user's skin, the seating spacer width $S_W$ can be provided in different lengths and widths to allow a more customized fit by the user which is conveniently determined at the point of use. For example, an adapter kit can be packaged for use with a particular application or inhaler, and can include seating spacers with three different widths $S_W$ to provide a more customized penetration distance for the user (such as 5 mm, 10 mm, and 20 mm seating spacers). In addition, the seating spacers 35 can be shaped with alternative configurations for different sized openings (such as 10, 20, and 30 mm).

The seating spacer 35 shown in FIG. 2 can be easily interchanged, as it is easily slidably attached to the tubular body 30b. Preferably, the seating spacer 30 is formed or coated with a material that allows a sliding but secure attachment to the tubular body 30b. For example, the seating spacer can be formed of nylon, of silicone, or the like. As is also shown in FIGS. 3A–3C, the adapter 30 can include an outwardly (radially) extending ledge 31 upon which the seating spacer 35 can slidably advance to rest against to provide a reliable alignment configuration and thereby also influence the penetration depth of the tubular body 30b.

Figure 4:
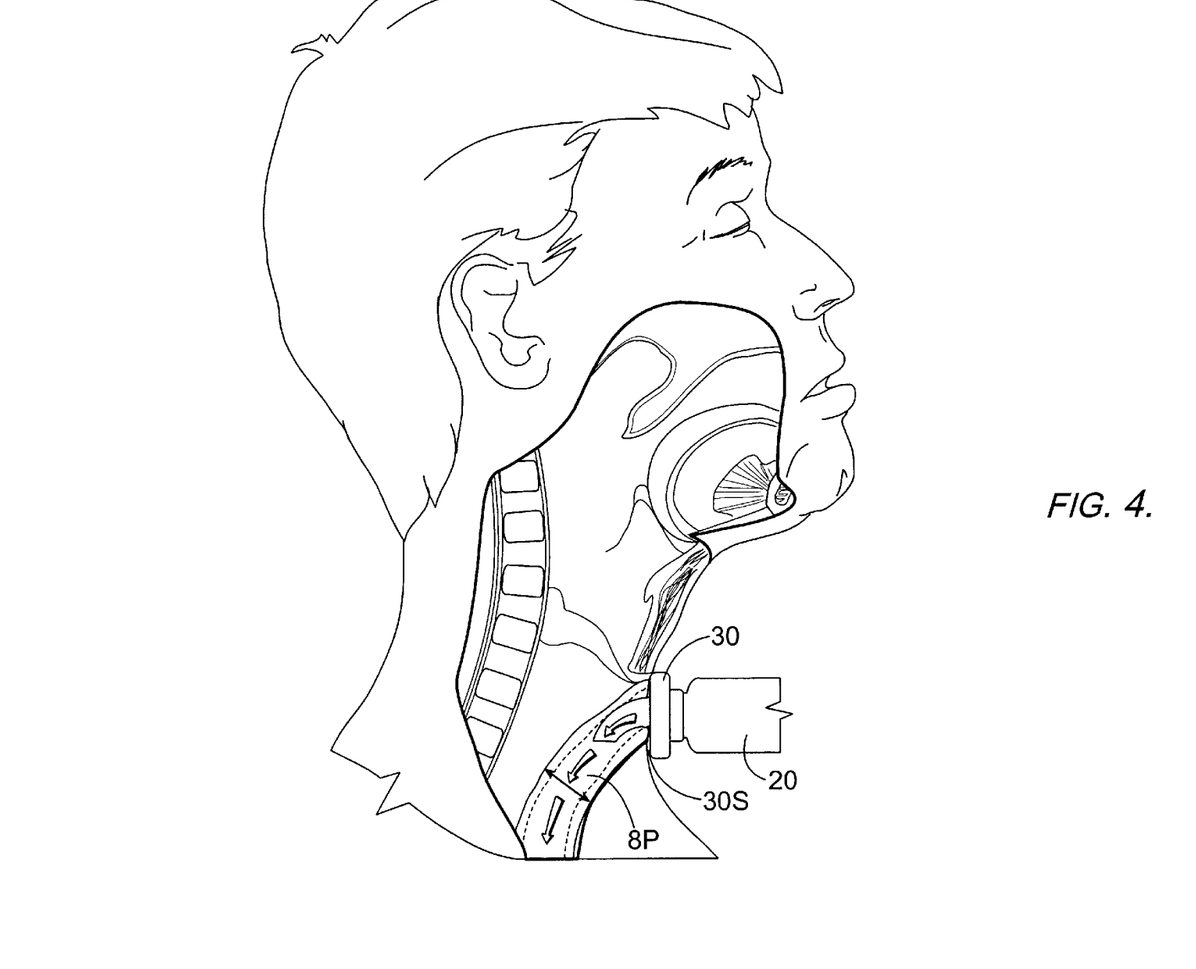
FIG. 4 is a side view of an alternate embodiment of an adapter according to the present invention inserted into a laryngectomized subject.

Alternatively, the tubular body 30b can be formed with an integral seating spacer portion such as with a stepped portion 30s as shown in FIG. 4. Of course, as noted above, the adapter 30 can be used without a seating spacer.

Figure 5:
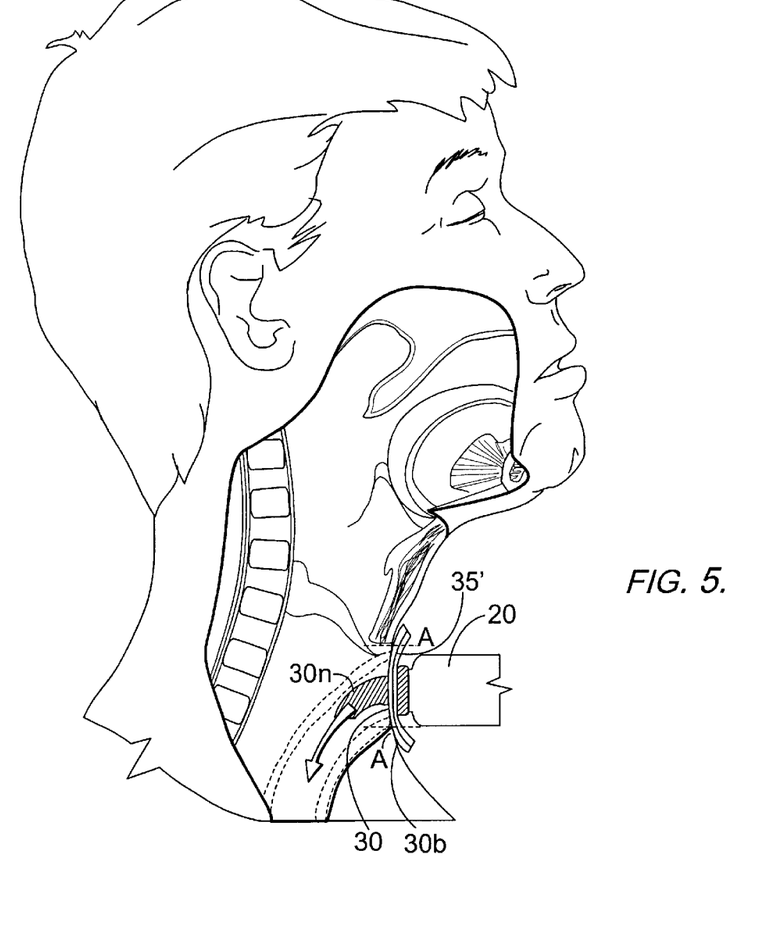
FIG. 5 is a side view of another alternate embodiment of an adapter according to the present invention inserted into a laryngectomized subject.

The adapter 30 may also be configured to engage with padding or other sealing layers to help reduce "jiggle" and/or to promote proper positioning and operation of the adapter 30. In one alternative embodiment, as shown in FIG. 5, the adapter 30 is configured with at least one relatively thin, conformable seating spacer 35' which is configured to substantially conform to (i.e., take on the shape of) the underlying body as it resides thereagainst and to extend across the opening (across points A–A'). As before, the conformable seating spacer 35' is preferably configured to tightly engage with the tubular body 30b and to seal the opening of the user thereto. As shown, the conformable seating spacer 35' has a concave contour. The conformable seating spacer 35' can be positioned on a user prior to inserting the adapter 30, or can be attached to the adapter first. FIG. 5 also illustrates a nozzle 30n exiting the tubular body 30b which has an elongated configuration.

Figures 6, 7:
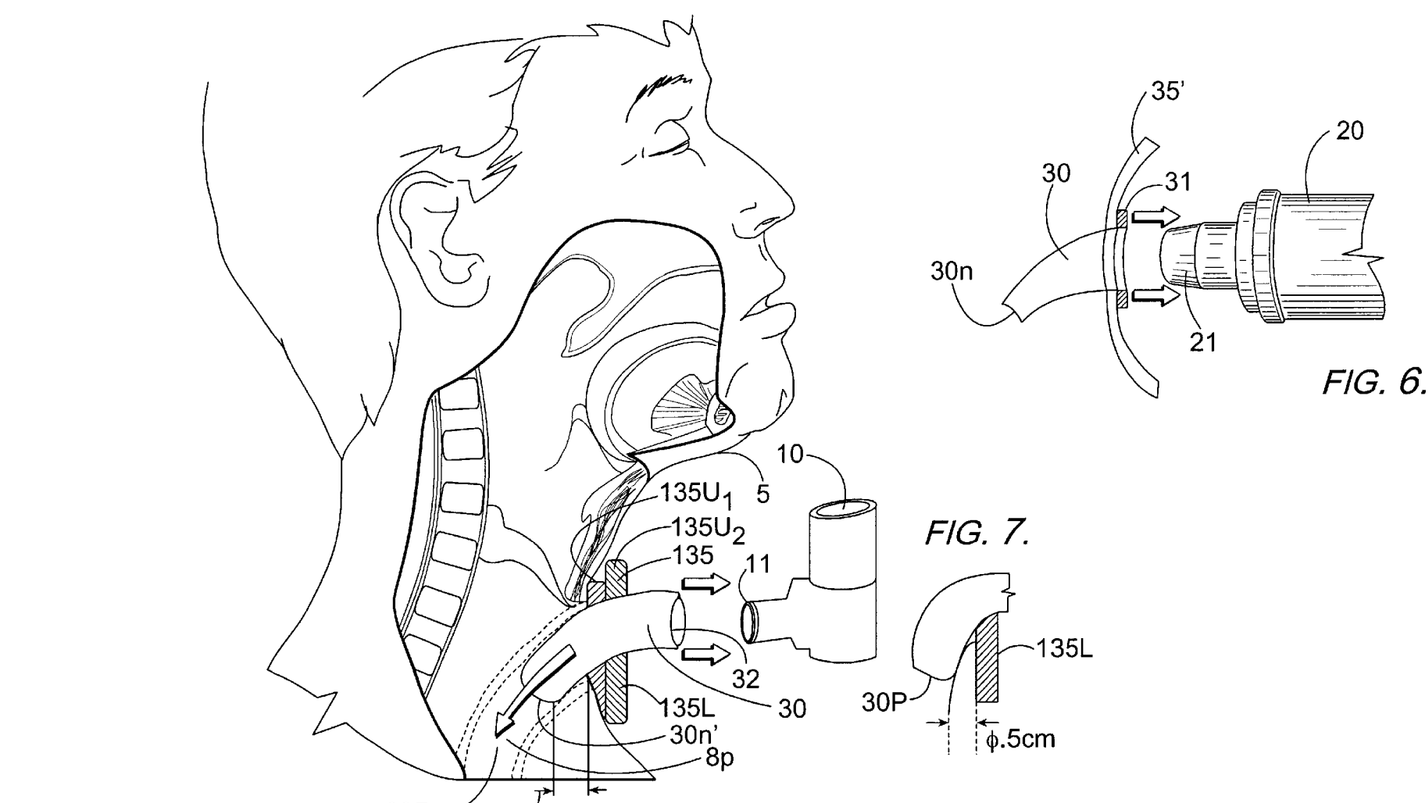
FIG. 6 is a side view of an embodiment according to the present invention similar to that shown in FIG. 5 with a conformal skirt extending from the adapter body.
FIG. 7 is a side view of yet another embodiment of an adapter according to the present invention which includes conformable material positioned proximate the neck opening.

FIG. 6 illustrates the conformable seating spacer 35' of FIG. 5 attached to the adapter body 30b proximate the ledge 31. The conformable seating spacer 35' can also include a releasable adhesive formed thereon to help secure it to the user. Of course, this may require more frequent interchange or replacement of the conformable seating spacer 35' to inhibit degradation of the seal due to environmental exposure to body and drug moistures during use. Thus, a plurality of conformable seating spacers, which can be adhesively secured to and released from the skin, may be desirable for each adapter or for each inhaler dispenser as the dispensers are typically filled with a plurality of doses. Double-sided tape, as well as other suitable adhesives for releasably securing medical devices to a patient, are known to those of skill in the art.

FIG. 7 illustrates another alternative embodiment, an adapter 30 used with at least one padding layer 135 which is preferably formed of a substantially conformable material and can, as discussed before, be attached to the patient or the adapter 30. As shown, the at least one padding layer 135 has an upper portion with two layers 135u1, 135u2 and a lower portion with one 135l. In this embodiment, the adapter 30' is a substantially elongated cylindrical tube or conduit, which extends through the opening 8 and into the air passage 8p of the user. Preferably, the adapter 30' is arcuately shaped or flexible so that as it enters the body through the opening it bends corresponding to the shape of the air passage. It is also preferred that, in position in the airway, the proximal side of the adapter penetration end 30p transversely extends beyond the padding a distance of about 0.5 cm relative to the lower or bottom padding 135l positioned about the opening 8. The second end portion 32 (the end proximate the inhaler or valved holding chamber/reservoir) is preferably resiliently configured and sized to stretch over and tightly engage with the desired mouthpiece and seal against the associated configuration of same (which may vary as noted above). The padding layer(s) 135 is configured and sized with an aperture which is aligned with the opening in the user 8 and sized to securely receive the adapter body 30b' therein. It should be noted that the padding layer 135 can be used with the seating spacer 35. FIG. 7 also illustrates that the adapter 30' is attachable directly to the mouthpiece 11 of an pMDI 10. The padding and/or the conformable seating spacers may comprise neoprene or similar materials.

Figure 8:
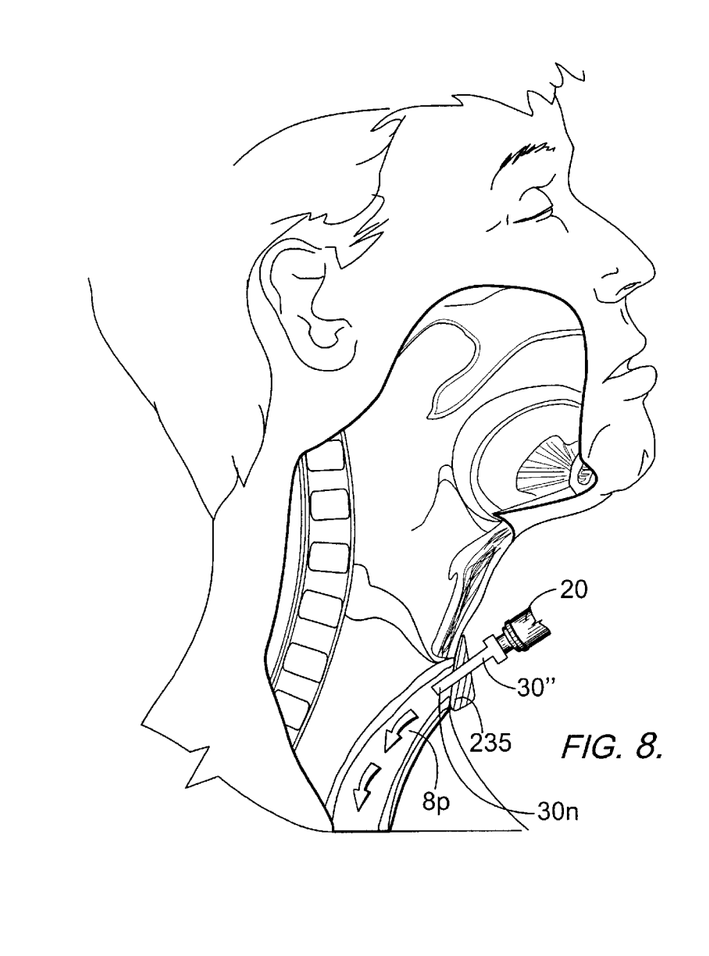
FIG. 8 is a side view of an additional embodiment of an adapter according to the present invention inserted into the opening in the neck of a laryngectomized subject.

FIG. 8 illustrates an adapter 30" having a generally straight linear configuration. Preferably, as is also shown, the seating spacer 235 is angled with respect to the surface of the opening 8 to provide the desired orientation of the adapter body (and more particularly the exit nozzle 30n) as the wedged or inclined seating spacer 235 rests against the skin or surface of the user proximate the opening 8; this portion allows the front end portion 33 of the adapter 30" to enter the opening 8 at the desired orientation or angle of inclination and extend into the air passage of the user 8p to direct the medication generally downward toward the pulmonary region.

Figure 9A:
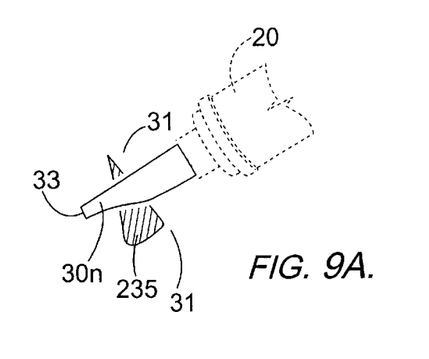
FIG. 9A is a side view of an embodiment of the present invention which is similar to that shown in FIG. 8, but with the adapter configured with a tapered nozzle end.
Figure 9B:
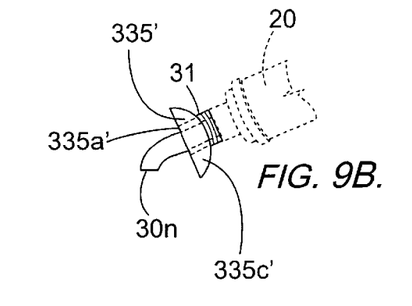
FIGS. 9B and 9C are side views of additional embodiments of adapters of the present invention with concave shaped conformable skirts preferably configured to substantially sealably engage with the user's skin and to seat or position the inserted end a sufficient depth into the subject. The circled numbers 1 and 2 in FIG. 9C illustrate the adapter of the present invention being oriented and then inserted into the neck opening of the user.
Figure 9C:
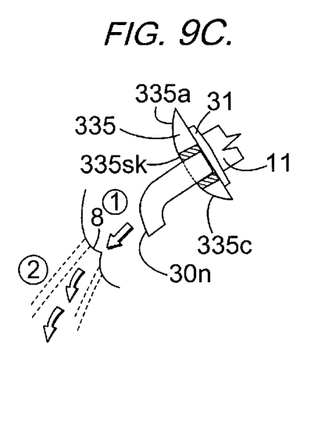

FIGS. 9B and 9C illustrate alternative seating spacers 335, 335' which can be attached and sealably engaged to the adapter 30. As shown, each of the seating spacers 335, 335' has a concave contour, one facing the opening 8 and one facing away from the opening 8. The seating spacers 335, 335' can be formed from one or a combination of materials. For example, a first layer 335a, 335a' (the layer contacting the skin) can be formed of an adhesive-skin release layer. Another or second layer can be formed of a conformable material (such as neoprene) layer 335c, 335c' with a central more rigid attachment skeleton or rib portion 335sk, 335sk' adjacent the tubular body 30b. The skeleton portion 335sk, 335sk' is preferably formed of an inexpensive but more rigid material relative to the conformable material, such as nylon which can bond with or attach to the conformable material 335c, 335c' to help keep hold the seating spacer held together and in position on the adapter body.

As the adapter tubular body 30b is inserted into the body's air passage 8p, it is preferred that it be coated or formed with a hypoallergenic and/or biocompatible material. It is also preferred that the adapter 30 be removably attached to the mouthpiece of the valved holding chamber or inhaler 21, 11 so that it can be conveniently periodically cleaned without undue hardship or specialized tools.

The present invention adapts the standard oral pMDI's or DPI's and/or associated valved holding chamber devices to be able to be relatively easily converted for use on laryngectomized subjects. It is anticipated that these subjects will be able to more effectively take advantage of the economies of scale provided by larger treatment populations without necessitating high-cost customized treatment inhalers for a relatively small segment of the population and still obtain treatment benefits accorded by improved delivery.

Advantageously, the present invention configures the adapter 30, 30' to enter the opening 8 a sufficient operative depth such that it can facilitate operation of the inhalant even if the trachea collapses during delivery.

In operation, the penetration depth and/or the flow channel 34 size and length defined by the adapter 30 as it is used with either the inhaler directly or with the valved holding chamber 20 may be important for influencing air/medication flow direction as well as proper dispersion of the drug into the air passage (inhibiting premature deposit of the drug) and/or to orient the device such that it reaches the desired systemic or target region.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A tracheostoma nozzle configured to deliver medicament to a user having a tracheostoma, said nozzle adapted to direct aerosolized medicament into the user's pulmonary system through the tracheostoma, wherein said nozzle is sized and configured to inhibit deposition of the aerosolized medicament in the nozzle and to discharge the medicament generally downwardly passage.

2. A tracheostoma nozzle according to claim 1, wherein said nozzle is configured to engage an inhaler device and define a unidirectional flow path and is adapted to be repeatedly inserted into and removed from the tracheostoma for episodic delivery of medicament into the user's pulmonary system, and wherein, in position, a lower end of the nozzle is configured to enter the tracheostoma to release the medicament substantially without expanding the local air passage and the lower end of the nozzle to thereby inhibit damage to the trachea and/or air passage during use.

3. A tracheostoma nozzle according to claim 1, wherein, in position, said nozzle is adapted to be able to be used in isolation of a tracheostomy tube.

4. A tracheostoma nozzle according to claim 2, wherein the inhaler device is a pressurized metered dose inhaler.

5. A tracheostoma nozzle according to claim 2, wherein the inhaler device is a dry powder inhaler.

6. A tracheostoma nozzle according to claim 1, wherein the nozzle is configured to releaseably engage an inhaler mouthpiece, and wherein the nozzle is configured and sized so that, in position, an internally held portion of said nozzle is substantially centered in an air passage of the user proximate the tracheal wall at the tracheostoma.

7. A tracheostoma nozzle according to claim 1, wherein said nozzle has an arcuate profile such that, during use, an arcuate portion of said nozzle extends into and penetrates through the tracheostoma in the user so as to direct the medication from the dispensing device generally downwardly in a direction away from a head of the user toward the user's pulmonary region into a user's air flow path as the medication exits said nozzle.

8. A tracheostoma nozzle according to claim 1, wherein said nozzle has opposing first and second end portions and a substantially tubular body with a curvilinear profile, said nozzle first end portion defining an exit flow port that is substantially circular in cross-section and has an open end, wherein said nozzle tubular body has a cross-sectional width which gradually turns and narrows from said second end portion to said first end portion such that said first end portion has a reduced width relative to said second end portion, said second end portion having a cross-sectional width of between about 8–14 mm, and wherein, in operation, said nozzle is configured to discharge the medicament in substantially laminar flow.

9. A tracheostoma nozzle according to claim 1, wherein said nozzle is configured to direct the medicament to exit said nozzle in a direction which is about 75–90 degrees away from the direction the medication travels as the medication enters said nozzle.

10. A tracheostoma nozzle according to claim 8, further comprising a seating spacer that is positioned intermediate said first and second end portions of said nozzle, wherein said seating spacer is configured such that, when in position, said seating spacer is spatially separated a distance away from said first end portion of said nozzle so as to allow sufficient penetration of said first end portion of said nozzle into the tracheostoma of the user such that the medication can be directed into the user air flow from said first end portion even if the trachea of the user collapses during use, and wherein the seating spacer is sized and configured to cover the tracheostoma to inhibit premature deposit of the medicament in local tissue and/or discharge from the tracheostoma during use.

11. A tracheostoma nozzle according to claim 10, wherein said seating spacer has a perimeter portion that is substantially conformal to the underlying skin of the user proximate the tracheostoma and is releaseably sealable against the skin of the user upon inhalation.

12. A tracheostoma nozzle according to claim 8, further comprising a plurality of releaseably securable and user selectable seating spacers, each of which has an aperture which is sized and configured to slidably receive said first end portion of said nozzle therethrough.

13. A tracheostoma nozzle according to claim 10, wherein the tracheostoma has an associated perimeter and said seating spacer is configured and shaped such that it extends a distance beyond the tracheostoma perimeter and is releaseably sealable against the skin of the user upon inhalation.

14. A tracheostoma nozzle according to claim 13, wherein said seating spacer is sized and configured to cooperate with said nozzle to define the orientation of the nozzle when in position in the user.

15. A tracheostoma nozzle according to claim 8, wherein said nozzle comprises a skirt element which, in position, resides against the user's skin proximate the entrance to the tracheostoma, and wherein said skirt element helps to hold said nozzle in position such that said skirt element provides a desired orientation of a flow path defined by the nozzle when said first end portion of said nozzle is inserted into the tracheostoma and said skirt element resides external thereof against the user's skin.

16. An inhaler-based delivery system for administering aerosolized medications to a user having a laryngectomy with an associated permanent tracheostoma neck opening extending through a tracheal wall to an internal air flow passage to allow breathing therethrough, comprising:
 a metered dose inhaler configured to discharge an aerosolized medicament, the inhaler having an exit port; and
 a tracheostoma nozzle having opposing first and second end portions and an internal flow path extending therebetween, wherein said internal flow path is in fluid communication with said metered dose inhaler to define a unidirectional flow path length that is between about 20–40 mm;
 wherein said nozzle first end portion is sized and configured to enter into the tracheostoma opening of the laryngectomized user a sufficient distance to direct the inhalant medication received from said metered dose inhaler through said nozzle internal flow path and generally downwardly into the user's air flow passage toward the user's pulmonary region.

17. A system according to claim 16, wherein said tracheostoma nozzle includes a seating spacer configured to engage a perimeter portion of said nozzle and adapted to reside intermediate said first and second end portions of said nozzle such that said seating spacer is held a distance away from said first end portion, and wherein, in position on the user, said seating spacer portion is configured and sized to reside against skin of the user external to the tracheostoma neck opening to define the internal penetration depth of said nozzle first end portion and to cover the tracheostoma neck opening to inhibit premature deposit of medication.

18. A system according to claim 17, wherein said nozzle second end portion is configured and sized to slidably engage with a pressurized metered dose inhaler, and wherein said nozzle is sized and configured to inhibit premature deposition of the medicament in the nozzle.

19. A system according to claim 18, wherein said nozzle second end portion is configured and sized to slidably engage with a valved holding chamber operably associated with the pressurized metered dose inhaler.

20. A system according to claim 16, wherein said nozzle has a substantially arcurate profile, and wherein, in operational position, an arcuate portion of the nozzle is configured to reside in the user on an internal side of the neck opening.

21. A system according to claim 18, wherein said nozzle has a length and is substantially cylindrical and substantially circular in cross-section across the length thereof with a curvilinear profile, said nozzle having opposing primary inner and outer surfaces, wherein said nozzle has a radially extending ledge positioned about a portion of the outer surface of said nozzle intermediate said first and second end portions, and wherein, in position, the lower end portion of the nozzle is configured to enter the tracheostoma to release the medicament substantially without expanding the local air passage and/or tracheostoma to thereby inhibit damage to the trachea and/or air passage during use.

22. A system according to claim 16, wherein said nozzle second end portion comprises an outwardly extending ledge, said system further comprises a seating spacer and an aperture, said aperture sized and configured to receive said nozzle first end portion therethrough, wherein said seating spacer is slidably engageable with said nozzle and positioned to abut said ledge and substantially sealably reside against an exterior portion of said nozzle theareat, wherein, in position on a user, said seating spacer externally abuts skin of the user proximate the tracheostoma such that said seating spacer releasably sealably engages with the skin of the user and inhibits premature deposit of the medication directed from said pressurized metered dose inhaler through said nozzle internal flow path.

23. A method of using a medication dispensing device for a subject having a tracheostoma, comprising:
providing a tracheostoma nozzle having first and second end portions and an internal flow path therebetween to a laryngectomized subject having a tracheostoma;
sliding the nozzle onto a dispensing device configured to dispense inhalable aerosolized medication;
inserting the nozzle first end portion into the user air flow passage through the trachestoma to a desired penetration depth such that the second end portion resides proximate to a tracheal wall of the subject in an air flow passage proximate the tracheostoma;
releasing medication from the dispensing device;
directing the medication into the nozzle and then directly into the user air flow passage such that the medication travels generally downwardly toward the user's pulmonary system; and
removing the nozzle from the tracheostoma;
wherein the inserting, directing and removing steps are repeatedly carried out by the user to episodically deliver inhalable medication.

24. A method according to claim 23, further comprising providing a conformal material such that said conformal material is aligned with the nozzle and the user to reside externally against the skin of the user during operation, and wherein, in position, a lower end of the nozzle is configured to enter the tracheostoma to release the medicament substantially without expanding the local air passage to thereby inhibit damage to the trachea and/or air passage during use, and wherein the directing step is carried out so as to discharge the medication in substantially laminar flow into the user.

25. A method according to claim 23, wherein said nozzle has an arcuate profile with a curved portion residing in the user during operation, and wherein the dispensing device comprises a pressurized metered dose inhaler with a mouthpiece, and wherein said sliding step is carried out by sliding the nozzle onto the mouthpiece thereof.

26. A method according to claim 23, wherein the dispensing device comprises a pressurized metered dose inhaler and a valved-holding chamber configured to aerosolize a medication, with a mouthpiece in fluid communication therewith, and wherein said sliding step is carried out by sliding the nozzle onto the mouthpiece thereof.

27. A laryngectomy modification kit for oral inhaler systems, comprising:

a tracheostoma nozzle having a curvilinear profile and a tubular body with opposing first and second end portions, said second end portion configured to slidably engage a mouthpiece associated with an oral inhaler system, wherein a curved portion and said first end portion is configured to reside in a subject on an internal side of a tracheostoma neck opening to discharge inhalable aerosolized medicament from the inhaler in a generally downward direction in the subject; and at least one spacer adapted to receive a portion of the nozzle therethrough and reside externally against the skin of the subject adjacent the tracheostoma neck opening to facilitate proper positioning and to cover the tracheostoma neck opening to inhibit premature deposit of the medicament in and/or from the user, wherein said nozzle is configured to be episodically inserted into the tracheostoma neck opening in the subject.

28. A kit according to claim 27, wherein said nozzle has a penetration length into the tracheostoma sufficient to substantially centrally position the nozzle first end portion in the proximate air space between opposing tracheal wall segments in the user, and wherein the nozzle first end portion has an open configuration so that the first end portion resides in the subject with a cross-sectional exit width of between about 8–14 mm to promote laminar flow of the inhalable medicament through and/or from the nozzle.

29. A kit according to claim 27, wherein said nozzle has a flow path with a length that is between about 20–44 mm, and wherein said nozzle is sized and configured to inhibit deposition of the medicament in the nozzle.

30. A kit according to claim 27, wherein said nozzle is a unitary member.

31. A kit according to claim 27, wherein said nozzle has a profile with a gradual radius of curvature, an open discharge end, and a contour that defines an internal surface that inhibits turbulence in a flow path defined by the nozzle.

32. A kit according to claim 27, wherein said nozzle is configured with a proximal curved portion with a length of about 0.5 cm that, in position, extends beyond said spacer so that a proximal portion of said nozzle penetrates the tracheostoma to reside in the subject's air passage proximate thereto.

33. A kit according to claim 27, wherein said nozzle is configured for episodic use by the subject by directing the medication to exit the nozzle directly out of the nozzle into the subject's air passage.

34. A kit according to claim 27, wherein the nozzle is adapted to administer the inhalant medication without requiring a tracheostomy tube.

35. A tracheostoma nozzle having opposing first and second ends and a tubular body therebetween, the nozzle configured to securely engage, and receive medicament from, an inhaler to deliver to deliver medicament to a user having a tracheostoma, said nozzle adapted to direct medicament into the user's pulmonary system through the tracheostoma, wherein said nozzle has an arcuate profile such that during use, said nozzle extends into and penetrates through the tracheostoma in the user so as to direct the medication from the dispensing device generally toward the user's pulmonary region directly into a user's air flow path as the medication exits said nozzle, and wherein, in operation, said nozzle is sized and configured to inhibit deposition of the medicament in the nozzle, define a unidirectional exit flow path, and to allow the medicament to substantially laminarly flow therethrough.

* * * * *

UNITED STATES PATENT AND TRADEMARK OFFICE
CERTIFICATE OF CORRECTION

PATENT NO. : 6,701,928 B2
DATED : March 9, 2004
INVENTOR(S) : Rubin et al.

It is certified that error appears in the above-identified patent and that said Letters Patent is hereby corrected as shown below:

Column 10,
Line 59, should read as follows -- toward the user's pulmonary system. --

Column 11,
Line 2, should read as follows -- damage to the trachea. --
Line 53, should read as follows -- cover the tracheostoma to inhabitat least one of premature deposit of the --
Line 54, should read as follows -- medicament in local tissue or discharge from the tra- --

Column 13,
Line 6, should read as follows --passage or tracheostoma to thereby inhabit damage to --
Line 7, should read as follows --the trachea. --
Line 9, should read as follows -- said system further comprises a seating spacer with --
Line 50, should read as follows -- inhabit damage to the trachea or air passage during use, --

Column 14,
Line 29, should read as follows -- a flow path with a length that is between about 20-40 mm. --
Line 64, should read as follows -- rectional exit flow path, and to generate a --
Line 65, should read as follows -- substantially laminarly flow of medicament. --

Signed and Sealed this

Thirty-first Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,701,928 B2
DATED : March 9, 2004
INVENTOR(S) : Rubin et al.

It is certified that error appears in the above-identified patent and that said Letters Patent is hereby corrected as shown below:

Column 11,
Line 53, should read as follows -- cover the tracheostoma to inhibit at least one of premature deposit of the --.

Column 13,
Line 6, should read as follows -- passage or tracheostoma to thereby inhibit damage to --.
Line 50, should read as follows -- inhibit damage to the trachea or air passage during use, --.

Signed and Sealed this

Sixth Day of September, 2005

JON W. DUDAS
*Director of the United States Patent and Trademark Office*